a12) United States Patent
Moler et al.

(10) Patent No.: US 6,729,196 B2
(45) Date of Patent: *May 4, 2004

(54) BIOLOGICAL INDIVIDUAL SAMPLER

(75) Inventors: Christopher L. Moler, Richland, WA (US); Trent Wetherbee, Kennewick, WA (US); Patrick Call, West Richland, WA (US); Charles J. Call, Albuquerque, NM (US); Vanessa M. Kenning, Kennewick, WA (US)

(73) Assignee: MesoSystems Technology, Inc., Kennewick, WA (US)

( * ) Notice: Subject to any disclaimer, the term of this patent is extended or adjusted under 35 U.S.C. 154(b) by 352 days.

This patent is subject to a terminal disclaimer.

(21) Appl. No.: 09/775,872

(22) Filed: Feb. 1, 2001

(65) Prior Publication Data

US 2001/0029793 A1 Oct. 18, 2001

Related U.S. Application Data

(63) Continuation-in-part of application No. 09/265,619, filed on Mar. 10, 1999, now Pat. No. 6,267,016, and a continuation-in-part of application No. 09/265,620, filed on Mar. 10, 1999, now Pat. No. 6,363,800.

(51) Int. Cl.[7] .............................................. G01N 31/20
(52) U.S. Cl. ................................................... 73/863.22
(58) Field of Search ......................... 73/863.22, 28.05, 73/28.06; 96/413; 435/30, 34, 7.21, 7.31, 7.32; 422/83

(56) References Cited

U.S. PATENT DOCUMENTS

| | | | |
|---|---|---|---|
| 3,633,405 A | * | 1/1972 | Noll |
| 5,949,001 A | * | 9/1999 | Willeke ..................... 73/865.5 |
| 6,267,016 B1 | * | 7/2001 | Call et al. |
| 6,532,835 B1 | * | 3/2003 | Saaski et al. ............ 73/863.21 |

* cited by examiner

Primary Examiner—Robert Raevis
(74) Attorney, Agent, or Firm—Ronald M. Anderson

(57) ABSTRACT

A portable sampling unit capable of separating particulates, including biological organisms, from gaseous fluids such as air. A combined particle impact collector and fan is used to both move fluid through the sampling unit and to collect particulates. In one embodiment, the combined particle impact collector is a disposable unit that is removed and replaced with a fresh unit after each sampling period. The disposable unit is placed in a rinse station, where a liquid sample is extracted for later analysis. Alternatively, a disposable detection unit is incorporated in the sampling unit to provide real time detection of chemical toxins and/or biological pathogens. Preferably, the detector unit includes micro-fluidic channels so that a minimum amount of sample and test reagents are required. In another embodiment, the combined impact collector is integral to the sampling unit, rather than a separate disposable item.

101 Claims, 9 Drawing Sheets

Figure 1:
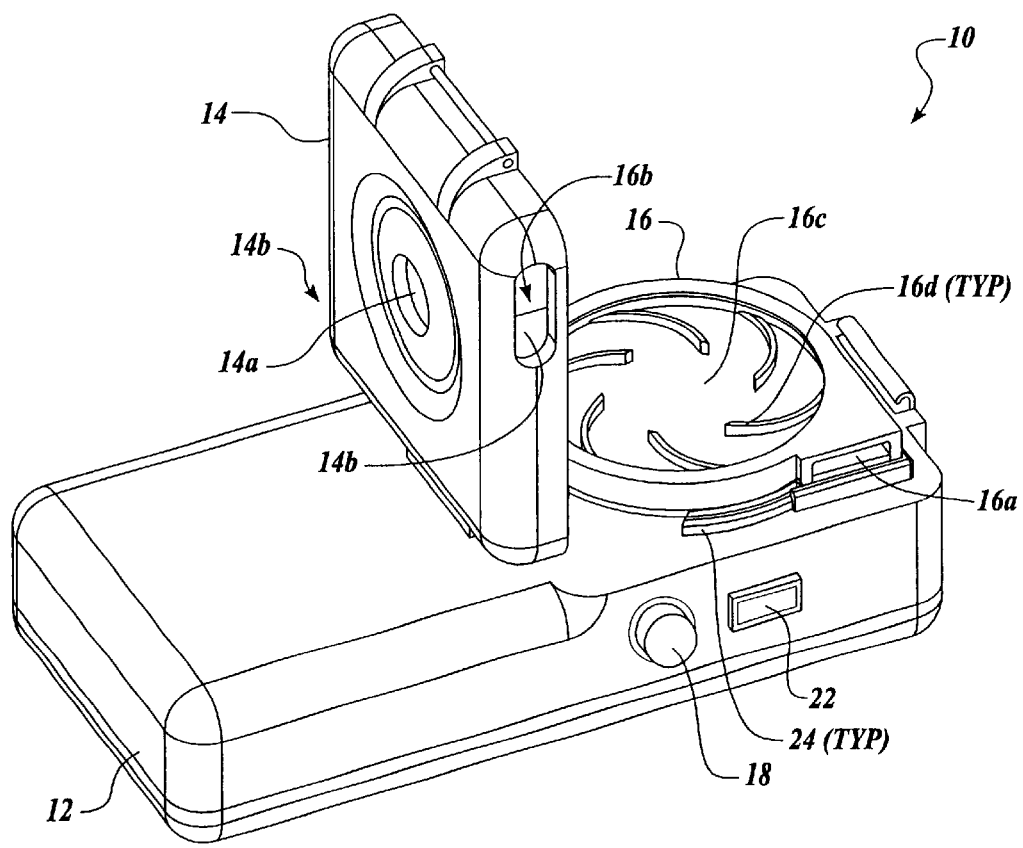

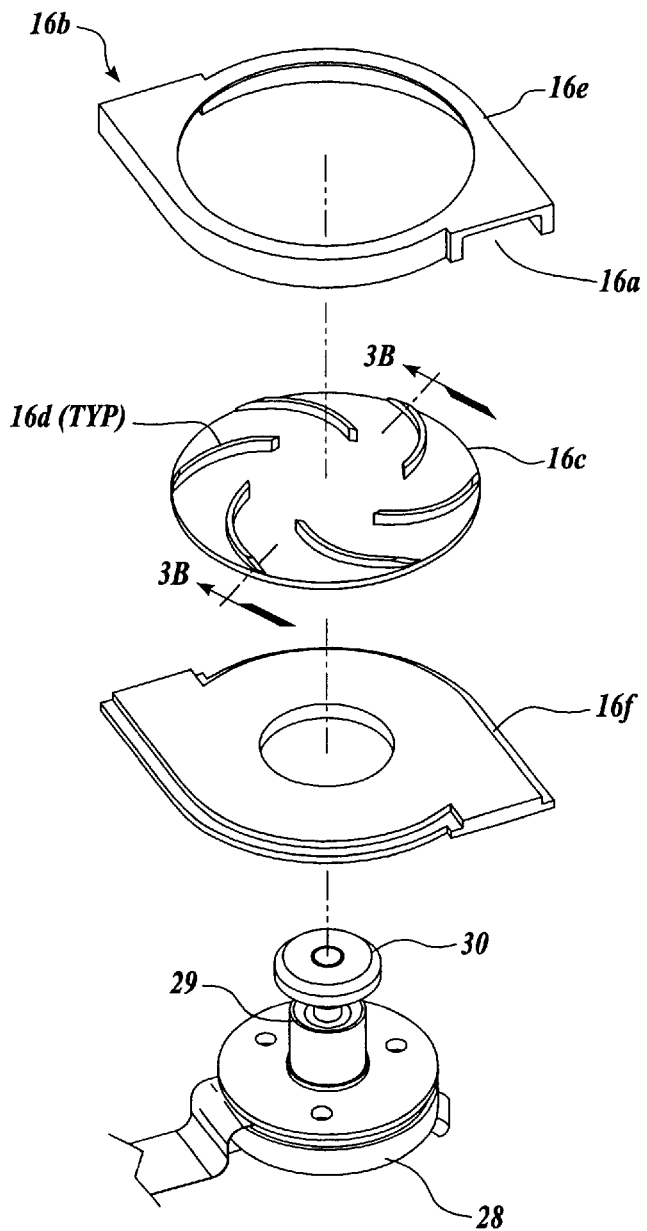
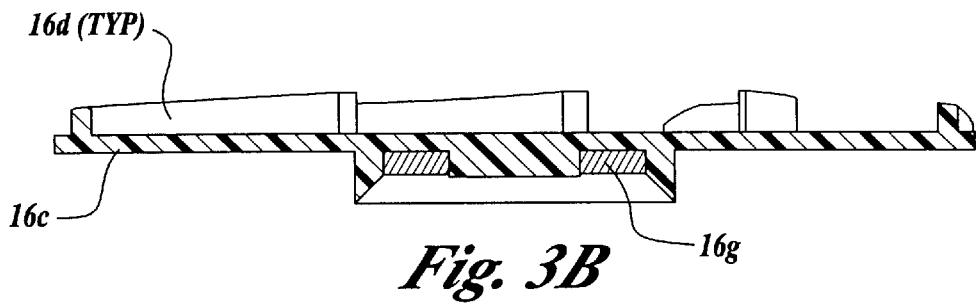
Fig. 3A
Fig. 3B

BIOLOGICAL INDIVIDUAL SAMPLER

RELATED APPLICATIONS

This application is a continuation-in-part of U.S. patent application Ser. No. 09/265,619 filed Mar. 10, 1999, now U.S. Pat. No. 6,267,016, and U.S. patent application Ser. No. 09/265,620, also filed Mar. 10, 1999, the benefit of the filing date of which is hereby claimed under 35 U.S.C. §120.

GOVERNMENT RIGHTS

This invention was made under contract with the United States Department of Defense, under Contract Nos. DAAM01-97-C-0036 and M67854-00-C-3023, and the United States government may have certain rights in the invention.

FIELD OF THE INVENTION

This invention generally relates to chemical sampling, and more specifically, to a man-portable chemical and biological sampler including a combination impact collector and fan, and integrated chemical and/or biological sensors.

BACKGROUND OF THE INVENTION

Sample acquisition and sample analysis are frequently performed as two disparate processes, since in situations that are not time critical, it is generally acceptable to take one or more samples, and to transport those samples to an analytical laboratory for analysis. Environmental air quality and water quality samples are often handled in such a fashion. However, there are many situations in which the ability to take an environmental air sample, and to analyze that sample immediately, are critical to health and safety. Measuring the air quality in poorly ventilated spaces such as mines, determining the presence of chemical and/or biological agents on the battlefield, or after an actual or suspected terrorist attack, are examples of situations in which sampling and analysis should be performed as quickly as possible, preferably by employing an integrated sampling and sensing apparatus that can provide and immediate indication of a life threatening substance in the environment.

There are many examples in the art of integrated sampling and detection apparatus. Dräger-Tubes, which are manufactured by Drägerwerk A G, Ltibeck (http://www.draeger.com), are one well-known example of an integrated sampling and detection system. These devices are used to measure the concentration of specific gases and vapors in real time. Over 200 different Dräger tubes are available for measuring more than 500 different contaminants. The design and principle of operation of each Dräger-Tubes is the same in every case. A chemical reagent system is housed in an enclosed clear glass tube; and the reagent system reacts by changing color when exposed to a specific gas or vapor. The concentration of the substance is characterized by the length of discoloration within the tube and can be read off directly from a scale printed on the glass tube. Different amounts of air must be drawn through the tube, depending on the type and sensitivity of the reagent systems used. The volume of ambient air that must be drawn through the tube by a Dräger pump is stated on each tube. This prior art chemical sampling and detection system thus consists of a Dräger-Tube and a corresponding Dräger pump.

Other integrated air sampling and detection systems specifically designed to detect trace gases in air include electrochemical sensors for the measurement of gases such as CO, $H_2S$, $O_2$, $Cl_2$, $SO_2$, $NO_2$ etc, infrared sensors for the measurement of $CO_2$, $CH_4$ or alkanes, and catalytic (pellistor) gas sensors for measuring flammable gases.

One drawback of the prior art integrated sampling and detection devices is that the target of interest is often present in the sampled environment in extremely small amounts. Acquiring a good sample of a reagent at low concentrations is problematic. Even if the sensor is capable of detecting minute levels of an agent of interest, without a high quality and readily obtainable representative sample, the capabilities of the sensing system are inefficiently utilized. Even worse, an inadequate sample of a hazardous material can cause a detection device to falsely indicate the absence of that material.

The difficulty in obtaining a good quality sample is particularly evident with respect to sampling for airborne particulates or aerosols. For example, aerosols comprising small droplets of liquid dispersed into air are not easily analyzed unless the aerosol materials are separated from the air and concentrated in a sample that can then be accurately analyzed. As used herein, the term "particulates" (and its singular form "particulate") will be understood to include aerosols, liquids, solids, or semi-solids that are sufficiently small to be dispersed within and carried about in air or other gases and may include inorganic or organic chemicals, or living materials, e.g., bacterial cells or spores. Also, the term particulates refers to solids or semi-solids introduced into a liquid that is then dispersed within air as an aerosol mist so that the solids are carried within the liquid droplets comprising the aerosol mist.

Generally, it is difficult to identify materials comprising particulates entrained in a gaseous fluid unless the particulates can be collected and concentrated in a specimen suitable for analysis by separating them from the air or other gaseous fluid. One significant application in which extremely low levels of particulates need to be sampled and analyzed quickly is to provide combat troops with individual sampling units, that either include their own sensor, or which can be read in the field under combat conditions.

Particle impact devices are commonly used for collecting particulates from gaseous streams in which they are dispersed. These collectors "sweep" a large volume of air, and concentrate any particulates collected to provide a high quality representative sample. Several different types of particle impact collectors are available. Functionally, these particle impact collectors generally employ circuitous paths with many abrupt changes of direction along the passages through which a particulate-laden fluid flows. The particulates, being substantially more massive than the molecules of the fluid in which they are entrained, fail to negotiate the abrupt turns in these passages and are thus separated from the moving fluid stream, collecting on the surfaces that they impact. In the presently available types of particle impact collectors, there is generally a trade off between simplicity and efficiency.

Stationary impact collectors that employ a fan to force air against the impact surface are relatively simple, but are somewhat less efficient than would be desired. Rotating arm collectors are more efficient, yet are also more complex, in that they require both the rotating impact collector and a fan to be independently driven.

It would therefore be desirable to provide a simple and efficient particle impact collector that is capable of yielding a high quality representative sample of particulates or aerosols. Such a device is described in commonly assigned, co-pending U.S. patent application, Ser. No. 09/265,619, entitled "Impact Particulate Collector Using A Rotary Impeller For Collecting Particulates And Moving A Fluid," which was filed Mar. 10, 1999, the specification and drawings of which are hereby specifically incorporated herein by reference. It would further be desirable to integrate such a sampling device with a sensor to provide a portable system capable of rapidly detecting the presence of an agent of interest, so that the sample that is collected does not need to be sent to a laboratory facility for analysis. The prior art does not teach or suggest a portable integrated sampler and sensor unit that employs a rotary impeller used to both collect particulates and move a fluid through the unit.

SUMMARY OF THE INVENTION

In accord with the present invention, a method and apparatus for separating particulates from a fluid are defined. A significant facet of the present invention is the use of a combined impact collector and fan, employed to both force a gaseous fluid into the sampling unit, and to provide an impact surface onto which particulates are impacted and collected.

According to the method of the present invention, a combined impact collector and fan is provided. The combined impact collector and fan is disposed within a cavity having a port and is rotatable about an axis. Rotation of the combined impact collector and fan draws a particulate-laden fluid into the cavity. Particulates are separated from the fluid when they impact on the combined impact collector and fan as it rotates. The combined impact collector and fan is then rinsed with a rinse fluid, and the "rinsate" (i.e., particulates from the combined impact collector and fan) are collected in the rinse fluid.

In at least one embodiment, the combined impact collector and fan is rinsed with the rinse fluid while it is rotating. Preferably, such an embodiment collects the rinsate in a rinse fluid reservoir, and the rinse fluid is recycled.

In a different embodiment, the combined impact collector and fan is rinsed with a rinse fluid only after the combined impact collector and fan has been rotated for a predefined period of time. Preferably, the predefined period of time is a function of the type of particulate being collected.

When the particulates being collected comprise biological organisms, the rinse fluid is preferably not toxic to biological organisms, so that a collected sample can be cultured to determine a result. However, this characteristic of the rinse fluid is unimportant and is not a requirement if the collected sample will be analyzed by methods other than culturing.

In another embodiment of the method of the present invention, the step of rinsing includes utilizing a rinse fluid that includes a surfactant to reduce a surface tension of the rinse fluid, thereby increasing an efficiency of the rinse fluid in carrying the rinsate away from the combined impact collector and fan during the rinsing step.

Preferably, in one embodiment, the combined impact collector and fan is a disposable element, so that the disposable element is removed from a prime mover that is included for rotating the combined impact collector and fan, before the rinse step. When employing such a disposable element, a rinse station is provided, and the step of rinsing includes the step of placing the combined impact collector and fan into the rinse station. Preferably, a rinse cassette is also provided, so that the step of placing the combined impact collector and fan into the rinse station includes the steps of inserting the combined impact collector and fan into the rinse cassette, and then placing the rinse cassette into the rinse station. In one embodiment, the step of rinsing includes the step of rotating the rinse cassette during rinsing, to aid in removing the particulates from the combined impact collector and fan. In another embodiment, the step of rinsing includes the step of applying an ultrasonic pulse to the rinse cassette during rinsing, to aid in removing the particulates from the combined impact collector.

In yet another embodiment, a decontamination fluid is provided, and the combined impact collector and the cavity are flushed with the decontamination fluid before rotating the combined impact collector. Preferably, the decontamination solution is either a bleach solution or a hydrogen peroxide solution. Any fluid lines in fluid communication with the combined impact collector and the cavity are also preferably decontaminated with the decontamination fluid.

A programmable electronic controller enables a user to selectively control a length of time during which the combined impact collector is rotating. A user is also enabled to selectively control the rinsing step, to selectively rinse either for a duration of the rotation of the combined impact collector, or to rinse after the combined impact collector has stopped rotating, or to rinse such that the rinsate is reused as a rinsing fluid, thereby recycling the rinsate. The user can also select a time period for the rinse. When a decontamination fluid is provided, a user is preferably enabled to selectively decontaminate the combined impact collector and the cavity prior to rotating the combined impact collector, or to decontaminate the combined impact collector and the cavity after rinsing and after the rinsate has been collected, or to decontaminate the combined impact collector and the cavity after a user-defined number of rotating, rinsing, and collecting cycles has occurred.

In still other embodiments, an analytical unit is included with the collector, and the method further includes the step of utilizing the analytical unit to test the rinsate. In one embodiment, the analytical unit includes a test strip capable of detecting anthrax. Preferably, the analytical unit is a disposable unit specifically adapted to detect a specific substance. In some embodiments, the analytical unit is a disposable micro-fluidic unit. One such micro-fluidic analytical unit employs a cytometry-based detection system, while another such analytical unit uses a fluorescence-based detection system.

Another aspect of the present invention is a portable impact particle collector for separating particulates from a gaseous fluid in which the particulates are entrained. Such apparatus includes a prime mover having a drive shaft that is drivingly rotated, a power supply capable of energizing the prime mover, and a primary housing that substantially encloses the prime mover and the power supply. This apparatus further includes a combined impact collector and fan that is coupled to the drive shaft and rotated thereby, and a fluid passage for conveying the gaseous fluid in which the particulates are entrained into the combined impact collector and fan. The fluid passage includes at least one inlet and at least one outlet. The apparatus further includes at least one user selectable control operatively connected to the prime mover, adapted to enable a user to selectively energize the prime mover.

In one embodiment, the combined impact collector and fan includes a plurality of arcuate-shaped vanes. Also, one configuration of the combined impact collector and fan includes a ferromagnetic element that is magnetically coupled to the prime mover.

In yet another embodiment, the combined impact collector and fan is disposed outside of the primary housing. Preferably, the primary housing then includes at least one surface feature to aid in positioning the combined impact collector and fan. A secondary housing substantially encloses the combined impact collector and fan and is preferably pivotally connected to the primary housing.

In one form of the present invention, the combined impact collector and fan is a consumable unit, adapted to be replaced by a user with a new unit after a defined period of use. In this form, the fluid passage and the combined impact collector and fan comprise an integrated unit. Preferably, the integrated unit includes a fluid passage fabricated from an upper portion and a lower portion of a housing, the combined impact collector and fan being disposed between the upper portion and the lower portion and being freely rotatable therein. Also preferably, at least one of the lower portion and the combined impact collector and fan are fabricated from a self-lubricating material to ensure that the combined impact collector and fan can freely rotate when disposed within the lower portion of the housing without requiring bearings or additional lubricants to reduce friction between the lower portion of the housing and the combined impact collector and fan.

In still another embodiment of the portable impact particle collector, an electronic controller is electrically coupled to the at least one control and to the prime mover. The electronic controller is substantially enclosed within the primary housing.

To aid in removing impacted particulates from the combined impact collector and fan, a rinse fluid reservoir adapted to contain a volume of rinse fluid and a first fluid line in fluid communication with the rinse fluid reservoir and the combined impact collector and fan is provided in one embodiment. Also included is a sample collection reservoir adapted to contain a volume of rinse fluid that has been used to rinse particulates from the combined impact collector and fan, and a second fluid line in fluid communication with the sample collection reservoir and the combined impact collector and fan.

A decontamination fluid reservoir, adapted to contain a fluid capable of decontaminating the combined impact collector, and a decontamination fluid line in fluid communication with the decontamination fluid reservoir and the combined impact collector and fan are included in one embodiment of the invention. The rinse fluid reservoir, the decontamination fluid reservoir, and the collection fluid reservoir are preferably disposed in a disposable fluid cartridge, which is substantially disposed outside the primary housing, while the first fluid line, the second fluid line, and the decontamination fluid line are substantially disposed within the primary housing. A plurality of valves and a pump are included so that a flow of fluid within the first fluid line, the second fluid line, and the decontamination fluid line can be independently controlled.

One configuration of the present invention includes a diagnostic cartridge, adapted to determine if the first fluid line and the second fluid line are functioning properly. Preferably, the diagnostic cartridge includes a plurality of fluid reservoirs. Markings on one or more of the fluid reservoirs indicate whether the first fluid line and the second fluid line are functioning properly.

The rinse fluid reservoir and the sample collection reservoir are combined into a single reservoir in another configuration of the present invention, such that the rinse fluid is recycled. Preferably, the rinse fluid includes water and may include a detergent to reduce surface tension, and to enhance the removal of particulates adhering to the combined impact collector. Optionally, the rinse fluid further includes a phosphate buffer solution capable of sustaining the viability of microorganism particulates, such that the microorganisms can be cultured.

In some embodiments, the combined impact collector is coated with a substance to which the particulates adhere when the substance is dry, the substance releasing the particulates when wetted with a rinse fluid. In some embodiments, the substance includes at least one of gelatin and sugar.

In embodiments of the present invention in which the combined impact collector is a disposable unit, a rinse station is preferably provided to enable a liquid sample to be removed from the combined impact collector. A rinse cartridge can be included to contain the disposable combined impact collector and any fluid used in the rinse station. The rinse station preferably includes either a prime mover to spin the disposable combined impact collector during rinsing, a vibrator to vibrate the disposable combined impact collector during rinsing, or an ultrasonic unit to apply an ultrasonic pulse to the disposable combined impact collector during rinsing, to aid in removing particulates from the combined impact collector.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1 is an isometric view of a portable sampler in accord with a first embodiment of the present invention;

FIG. 2 is an exploded isometric view of the embodiment of FIG. 1;

FIG. 3A is an exploded isometric view of a disposable sampling cartridge for use in the embodiment of FIG. 1;

FIG. 3B is a cross-sectional view of a combined impact collector and fan, taken along line 3B—3B of FIG. 3A;

FIG. 4A is an isometric view of a disposable rinse cassette employed when extracting a sample from the sampling cartridge of FIG. 3A;

FIG. 4B is an isometric view of a preferred embodiment of a rinse station employed to extract a sample from a sampling cartridge that is inserted into the rinse cassette of FIG. 4A;

FIG. 5 is an isometric view of a portable sampler and integrated sensor unit in accord with a second embodiment of the present invention;

FIG. 6A is an isometric view of a portable sampler unit in accord with another embodiment of the present invention;

FIG. 6B is a modified side view of the portable sampler unit of FIG. 6A, also showing a removable sample cartridge that is used with the unit;

FIG. 7 is an exploded isometric view of the portable sampler unit of FIG. 6A;

FIG. 8A is a front view of a diagnostic cartridge for use with the portable sampler unit of FIG. 6A;

FIG. 8B is a rear view of a diagnostic cartridge for use with the portable sampler unit of FIG. 6A; and FIG. 9 is an isometric view of a portable sampler and integrated sensor unit in accord with yet another embodiment of the present invention, and showing a removable detection unit that is used with the portable sampler.

DESCRIPTION OF THE PREFERRED EMBODIMENT

Overview

The present invention employs a combined particle impact collector and fan to both drive a gaseous fluid into a collection unit and to collect particulates. The combined particle impact collector and fan is readily fabricated in a sufficiently small size so as to enable it to be used in a portable collecting device that has the ability to process relatively large volumes of gaseous fluids in order to detect trace levels of contaminants. Several different embodiments are described below, including a collector in which the combined particle impact collector and fan is a disposable component and intended to be replaced after each use, as well as units in which the combined particle impact collector and fan is an integral component and adapted to be decontaminated and reused. A primary application of these collector devices is in monitoring ambient air to detect trace particulates and aerosols. Samples of particulates that are thus collected can be taken to offsite laboratories for analysis, or detection units can be integrated into the collection units for detecting specific substances in real time. The substances that are thus detectable may encompass a broad range of chemical and/or biological substances. For example, in accord with the present invention, chemical warfare agents or pathogens can be collected and identified by a field portable collector that includes an appropriate detection unit and is sufficiently small to be readily carried about by one person.

Personal Air-Monitoring Embodiment

A first embodiment of the present invention is illustrated in FIG. 1, which shows a functional prototype of a personal air-monitoring unit 10. It is anticipated that such a unit will fulfill a military requirement to assess an individual's potential exposure to harmful chemical and biological substances encountered in combat or as a result of terrorist activities. It should be noted however, that such a personal air-monitoring unit is expected to have wide spread application outside of military and law enforcement uses. For example, personal air-monitoring unit 10 might be used in hospitals, research facilities, and industrial facilities to detect exposure to dangerous substances that might be released into the environment due to accident. As potential exposure to airborne chemicals and biological organisms is relatively pervasive, it is contemplated that personal air-monitoring unit 10 will have widespread utility.

Personal air-monitoring unit 10 includes a primary housing 12, a secondary housing 14, a power switch 18, a battery charge indicator 22, and a disposable sample collection cartridge 16. Note that primary housing 12 includes a plurality of surface features 24 that help to correctly position disposable sample collection cartridge 16 on the primary housing. Secondary housing 14 includes an inlet air port 14a and an outlet air ports 14b. Inlet air port 14a overlies the center of a combined impact collector and fan 16c, while outlet air ports 14b correspond to outlet air ports 16a and 16b (see FIG. 2) on disposable sample collection cartridge 16. Combined impact collector and fan 16c (as configured in this embodiment) rotates in a clockwise direction, as viewed from above, and includes a plurality of arcuate vanes 16d that serve as impellers and provide rotating impact surfaces that collect particulates entrained within the air. Note that the direction of rotation is not critical, and that combined impact collector and fan 16c can also be rotated in a counterclockwise direction. As the combined impact collector fan rotates, typically at speeds in excess of 5,000 RPM, it draws ambient air through inlet air port 14a so that particulates can be separated from the air by impact with the surfaces of arcuate vanes 16d. It should be noted that the orientation of the outlet air ports 16a and 16b directs the exhaust air from which most of the particulates have been removed, to the sides of the unit.

Personal air-monitoring unit 10 is lightweight and designed to be worn by an individual for the purpose of monitoring the person's exposure to biological pathogens, or other airborne toxic particulates. Preferably, personal air-monitoring unit 10 is energized with a battery power supply and is sufficiently small in size and weight so as to minimize any inconvenience to the wearer. Power switch 18 can be selectively activated during a period of interest (such as while working in an area of potential contamination, or during a specific activity, such as while working with potentially ill patients, or in other areas where air quality or contamination is a concern). The personal air-monitoring unit can be de-energized to conserve battery life, when the wearer is no longer in an area of concern. Battery charge indicator 22 is included to warn a user of a low battery charge condition. It is contemplated that disposable or rechargeable batteries can be employed. While not specifically shown, it is contemplated that primary housing 12 will include mounting clips, to enable a user to mount personal air-monitoring unit 10 to a belt (or to clothing, a strap, or harness), much in the way a pager or other portable device is mounted. Such attachment might be completed with a clip, a buckled strap, a hoop/loop fastening strip, or other suitable fixtures, depending on a specific user's requirements. A functional prototype of the personal air-monitoring unit having an overall size of 4.5"×2.5"×1.3" has been developed. The overall weight of the functional prototype is less than 350 grams, and the weight of disposable sample collection cartridge 16 is less than 20 grams.

A different disposable sample collection cartridge 16 is needed for each sampling period. As will be described in detail below, the combined impact collector and fan is contained within each disposable sample collection cartridge. It is contemplated that each disposable sample collection cartridge will have a unique identifier (such as a barcode or RF tag—not shown), which specifically identifies each user. Preferably, once used, the disposable sample collection cartridge will be sealed in sterile packaging until opened for analysis. When the desired collection period has been completed (at the end of a work day, for example), the disposable sample collection cartridge is removed from personal air-monitoring unit 10 and is subjected to an analysis to detect biological or chemically hazardous particulates that may have been collected therein.

As will be discussed more in detail below, to facilitate analysis, a liquid sample must be obtained that includes particulates collected on the surfaces of arcuate vanes 16d. Thus, the disposable sample collection cartridge must be rinsed under controlled conditions to provide the liquid sample used in the analysis. The resulting particulate-laden rinse fluid will then be analyzed, and the sample collection cartridge safely discarded. The results, including information from the barcode (lot number, user, etc.) will preferably be displayed, documented, and transferred to a database for archival storage. With insertion of a new disposable cartridge and fresh batteries, the personal air-monitoring unit is ready to collect a new sample. Use of a disposable cartridge has the advantage of avoiding sample cross contamination without cumbersome decontamination procedures. A disposable also eliminates concerns of damage or reduced sample collection effectiveness that can be caused by decontamination procedures.

Figure 2:
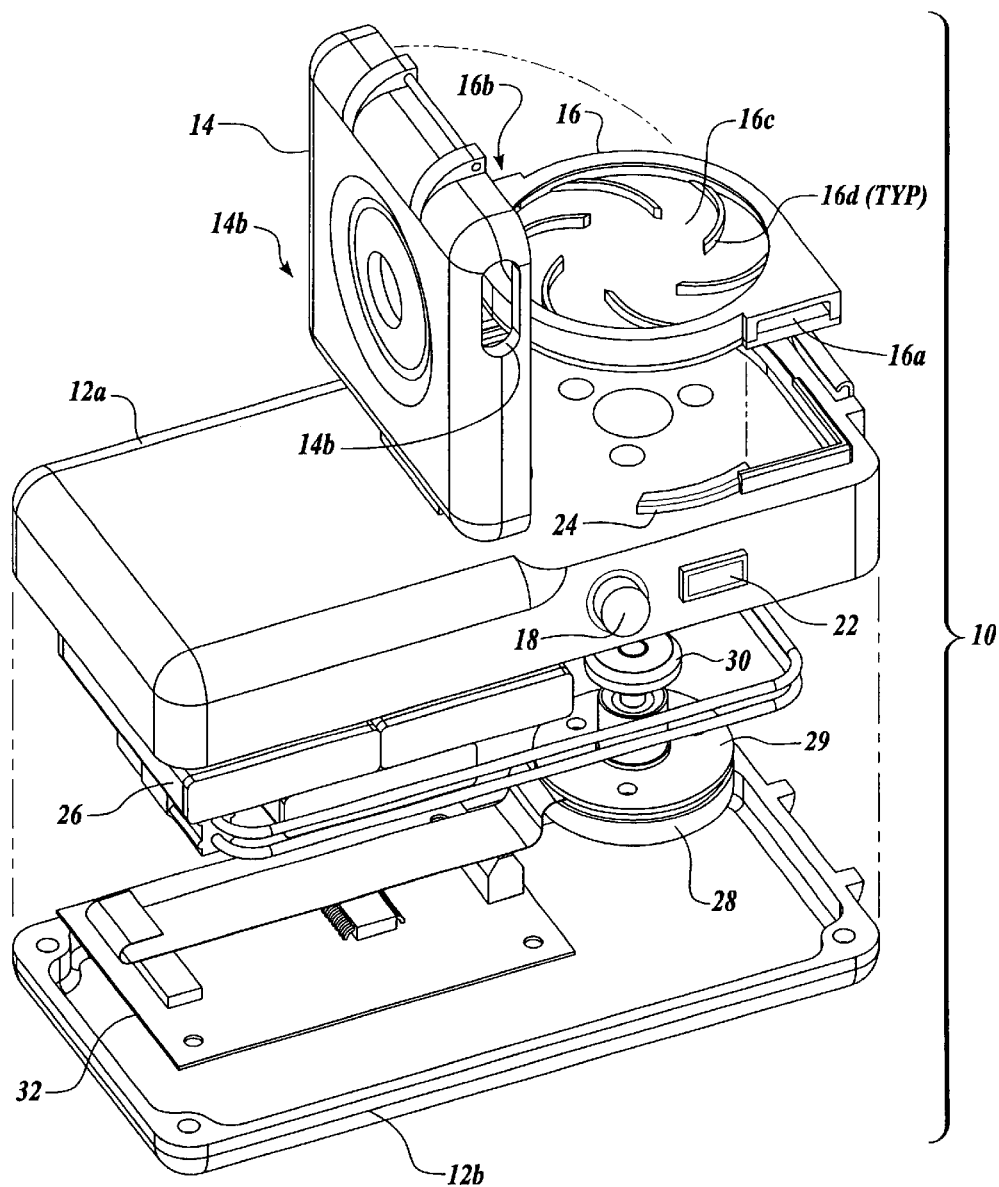

Referring now to the exploded view in FIG. 2, additional details of personal air-monitoring unit 10 are visible. Primary housing 12 includes an upper section 12a and a lower section 12b. These housing sections are preferably removably connected together so that internal components can be changed when required (for example, to replace disposable batteries). Batteries 26 (rechargeable or disposable) energize an electric motor 28. Preferably, batteries 26 are lithium ion or metal hydride batteries, and electric motor 28 is a brushless, direct current type. Battery tests with the prototype unit discussed above have indicated that to achieve a uniform performance of the device over at least eight hours of continuous use, alkaline batteries are inadequate due to a significant voltage drop that occurs as such batteries discharge.

A drive shaft 29 terminates in a magnetic coupler 30. Magnetic coupler 30 is magnetically coupled to a ferromagnetic element (see FIG. 3B) included in combined impact collector and fan 16c. This magnetic coupling enables disposable sample collection cartridge 16 to be readily removed and replaced with a new cartridge, and enables combined impact collector and fan 16c to be drivingly coupled to drive shaft 29.

An electronic controller 32 is electrically coupled to power switch 18, battery charge indicator 22, batteries 26, and electric motor 28. Empirical data indicates that the rotational speed of electric motor 28 has a substantial effect on the collection efficiency of combined impact collector and fan 16c. Electronic controller 32 controls electric motor 28 so as to optimize collection efficiency and battery life. Furthermore, it is anticipated that additional empirical data will indicate a relationship between specific particulates and the optimal rotational speed for combined impact collector and fan 16c. As more details concerning this relationship are determined, electronic controller 32 will preferably be programmed to maintain different optimum speed ranges for a variety of different particulates, such that when desired, personal air-monitoring unit 10 can be optimized for collecting a specific particulate of interest.

FIG. 3A provides a more detailed view of the components of disposable sample collection cartridge 16, and shows how combined impact collector and fan 16 is coupled to drive shaft 29. Disposable sample collection cartridge 16 comprises an upper shell 16e, a lower shell 16f, and combined impact collector and fan 16c, which is disposed between the upper and lower shells. Note that when assembled, upper shell 16e and lower shell 16f form a fluid passage having outlet air ports 16a and 16b. As combined impact collector and fan 16c is rotated by electric motor 28 (via drive shaft 29 and magnetic coupler 30), particulate-laden air is drawn into the central opening formed in upper shell 16e, so that the particulates entrained in the air impact on and adhere to arcuate vanes 16d, until removed by rinsing.

As shown in FIG. 3B and noted above, combined impact collector and fan 16c includes a ferromagnetic element 16g, which is magnetically coupled to magnetic coupler 30. Preferably, ferromagnetic element 16g is of a relatively low mass, so that it imposes very little additional load on electric motor 28; the smallest mass ferromagnetic element capable of ensuring positive magnetic coupling is employed. Of course, ferromagnetic element 16g must be carefully placed in the center of the combined impact collector and fan 16c so that rotation efficiency of combined impact collector and fan 16c is not adversely effected. Note that a ferromagnetic element 16g that is too massive will likely negatively effect battery life expectancy. In the prototype collector unit, a small iron washer was effectively employed for ferromagnetic element 16g.

Preferably upper shell 16e, lower shell 16f, and combined impact collector and fan 16c are fabricated from a plastic material. It is anticipated that injection molded components of suitable quality can be inexpensively produced in large quantities. Preferably, lower shell 16f and/or combined impact collector and fan 16c are fabricated from a plastic material that exhibits good self lubricating properties so that neither bearings nor additional lubricants are required to enable combined impact collector and fan 16c to freely rotate between the upper and lower shells.

Once disposable sample collection cartridge 16 has been collecting particulates for a desired period of time, the particulates need to be removed from combined impact collector and fan 16c for analysis. Preferably, a liquid sample that includes particulates, which were collected on the internal surfaces of the sample collection cartridge, will be prepared, as most analytical techniques are adapted to process liquid samples. While many techniques are known for preparing a liquid sample, the present invention preferably employs a rinse station specifically designed to prepare a liquid sample from a disposable sample collection cartridge 16.

In the most generic embodiment, the rinse station will use a known volume of rinse solution to extract a liquid sample from a disposable sample collection cartridge 16. To enhance rinsing, a wetting agent or surfactant can optionally be added to the rinse solution. It is anticipated that a heated rinse fluid will be particularly useful in cold environments. As the rinse station is to be field portable, it is likely that the rinse station will be employed in unheated conditions in cold climates. If the analytical technique to be employed is based on culturing biological organisms, then a rinse solution that is non-toxic to such organisms must be employed. Preferably, a phosphate buffer rinse solution will be used when applying such culturing techniques. Other contemplated rinsing enhancements that can be incorporated into the rinse station in accord with the present invention include an ultrasonic transducer that applies an ultrasonic pulse to the disposable sample collection cartridge during rinsing, or a vibration unit that vibrates the disposable sample collection cartridge during rinsing, or an electric motor that rotates the combined impact collector and fan in the disposable sample collection cartridge during rinsing. The vibration unit is discussed in greater detail below.

Figure 4A:
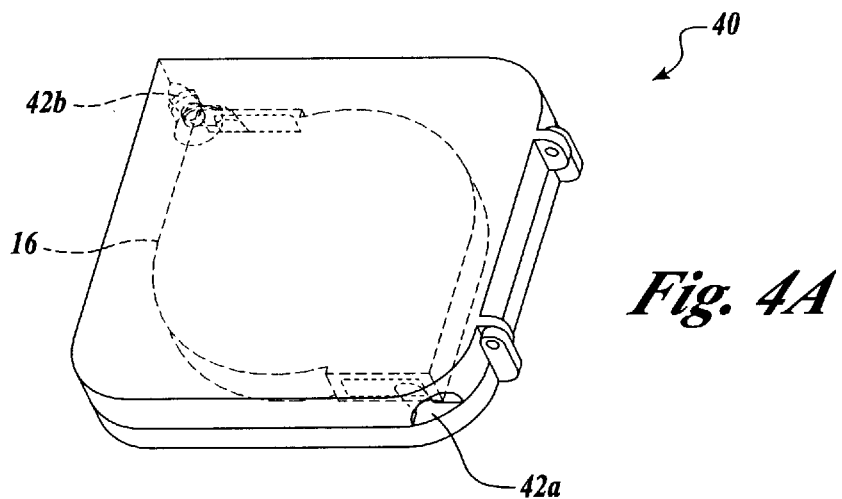
Figure 4B:
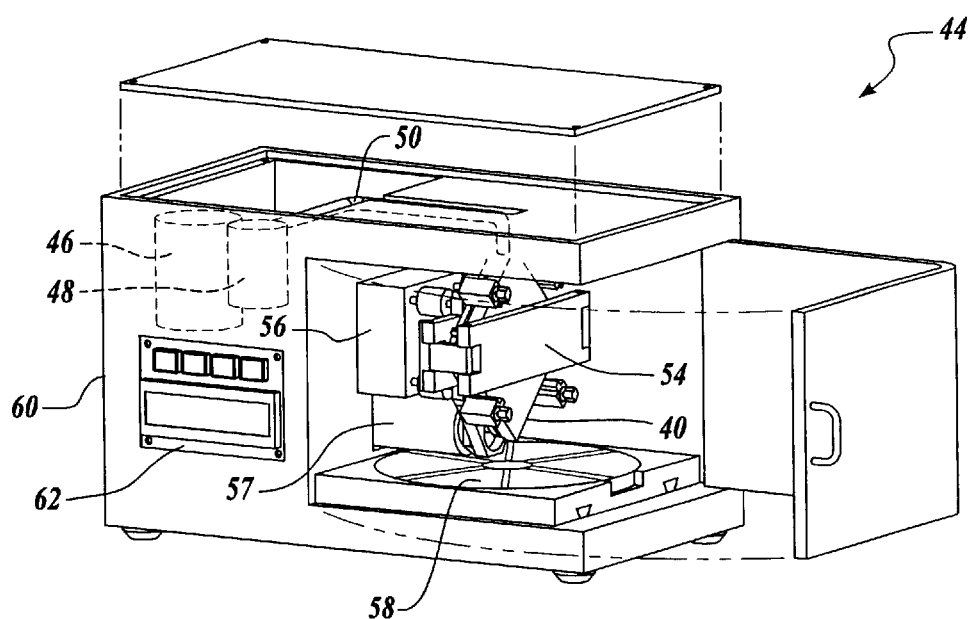

FIGS. 4A and 4B illustrate elements of a preferred rinsing station. In FIG. 4A, a rinse cassette 40 is shown, with a disposable sample collection cartridge 16 held inside the rinse cassette. Preferably an interior surface of rinse cassette 40 is contoured to approximately match the shape of disposable sample collection cartridge 16, thereby minimizing a volume of rinse fluid that will be injected into rinse cassette 40 during rinsing. Rinse cassette 40 includes a fluid port 42a through which the rinse fluid is injected into rinse cassette 40, and a fluid port 42b that includes an integral pinch valve. When the pinch valve is actuated after the rinsing step is complete, a sample of the rinse fluid containing particulates that have been rinsed from combined impact collector and fan 16c is removed from rinse cassette 40.

After the disposable sample collection cartridge 16 is inserted into rinse cassette 40, the rinse cassette is then inserted into a rinse station 44, illustrated in FIG. 4B. Rinse station 44 includes a rinse fluid reservoir 46, a fluid pump 48 that enables a precisely metered volume of rinse fluid to be injected into the rinse cassette, and a fluid line 50 is in fluid communication with fluid pump 48, rinse fluid reservoir 46, and rinse cassette 40 that is held in place by a bracket 54. Note that when rinse cassette 40 is properly positioned and latched in place by bracket 54, fluid port 42a of rinse cassette 40 is in fluid communication with fluid line 50. Thus, a precisely metered volume of rinse fluid can be injected into rinse cassette 40. Because the pinch valve associated with fluid port 42b is not actuated, rinse fluid injected into rinse cassette 40 will be retained within the rinse cassette until a sample is withdrawn by actuating the pinch valve.

Rinse station 44 also includes a vibration unit 56. When a rinse cassette has been placed into rinse cassette bracket 54 and filled with a precisely metered volume of fluid, vibration unit 56 is energized to vibrate the combined impact collector and fan disposed within rinse cassette 40. This vibration aids in removing adhered particulates from the surfaces of the combined impact collector and fan. It is contemplated that an ultrasonic transducer unit can alternatively replace vibration unit 56 to provide ultrasonic pulses that loosen the particulates from the surfaces of the collector.

Note that when a rinse cassette is properly positioned and held in place by bracket 54, fluid port 42b and its pinch valve are disposed immediately adjacent to a solenoid unit 57. Once the rinse cycle is complete, solenoid unit 52 is energized, and the pinch valve associated with fluid port 42b is actuated. Fluid port 42b of rinse cassette 40 is disposed immediately above a lateral flow disk 58. The rinse liquid injected into rinse cassette (carrying particulates removed from the combined impact collector) drains onto the lateral flow disk, where it is collected for analysis. It is anticipated that another type of sample collector, such as a vial or ampoule (not shown), will be placed under fluid port 42b to collect the sample.

Finally, rinse station 44 includes a housing 60 that substantially encloses rinse fluid reservoir 46. Pump 48 and solenoid unit 57 are also enclosed by housing 60, and lateral flow disk 58 and rinse cassette bracket 54 are enclosed by a removable screen or door 59. A control panel 62 enables a user to control pump 48, vibration unit 56, and solenoid unit 57 during the rinse cycle.

It should be noted that alternative embodiments of rinse cassette 40 and rinse station 44 are contemplated. It may be desirable to enable a sealed rinse cassette or the combined impact collector and fan to be rotated by an electric motor (not separately shown) during the rinse cycle, to further aid in the removal of attached particulates. Rinse cassette 40 could not be rotated in this fashion, as the rinse fluid would leak out of fluid port 42a during the rotation. A pinch valve (not separately shown) could be included in fluid port 42a, so that rinse fluid cannot enter or exit the rinse cassette unless the pinch valve is actuated. This modification would require either an additional solenoid (also not shown) to be included in rinse station 44 to actuate the added pinch valve associated with fluid port 42a. Alternatively, a fluid line in fluid communication with fluid port 42b, pump 48, and rinse fluid reservoir 46 could be added to rinse station 44, so that fluid port 42b would be used to both fill and drain the rinse cassette, eliminating the need for fluid port 42a, or an additional solenoid unit and pinch valve.

Figure 5:
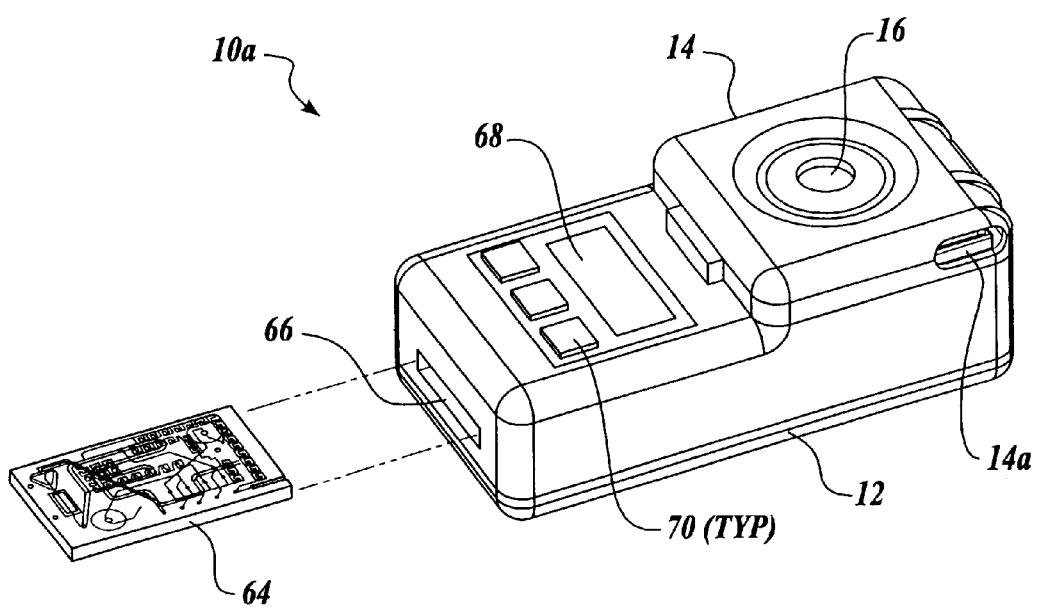

To minimize the volume of reagents required, and to minimize the amount of waste generated, it is preferred that small volumes of rinse fluid be employed. It is anticipated that 1–5 ml of rinse fluid represents a preferred range. However, it should be understood that more or less rinse fluid can be employed, depending on the nature of the particulates collected, the size of the disposable sample collection cartridge, and other factors. FIG. 5 illustrates a personal air-monitoring unit 10a. This embodiment incorporates a detection unit 64, which is capable of identifying a specific particulate of interest. Detection unit 64 is intended to be disposable and to be replaced at the same time as disposable sample collection cartridge 16, following its use in attempting to detect substances in the sample that was collected by the personal air-monitoring unit.

Note that detection unit 64 will be specifically designed to detect a particular chemical or microorganism (or a class of chemicals or pathogens), and will not be sensitive to non-target agents. Thus, if anthrax spores have been collected, but detection unit 64 is designed to detect nerve gas agents, the presence of anthrax will not be reported. While it would be preferable for detection unit 64 to be capable of detecting all types of particulates of interest, i.e., all chemical/biologically harmful agents, the state of the art of detection technology is not yet capable of implementing such a wide spectrum detector in a size that can be included in a portable and disposable detector. However, the state of the art of detection technology does offer a wide variety of detectors for specific substances that can be employed as compact and disposable units. These detectors can be fabricated to detect a specific substance or class of substances from a wide variety of different target substances. Preferably, detection unit 64 is adapted to detect at least either a chemical, a biological pathogen, a biological toxin, an allergen, a mold, or a fungi.

Preferably, detection unit 64 is configured in an elongate, relatively thin card shape and includes a plurality of micro-fluidic channels. Detection unit 64 will include all the reagents required to perform the desired analysis. The use of micro-fluidic architecture enables relatively small quantities of reagents to detect a substance in a relatively small amount of a sample, so that a compact detection system is readily implementable.

Such card based detection units have been developed by Micronics, Inc., based in Redmond, Wash. Micronics has developed several lab-on-a-chip technologies that are implemented as low-cost plastic, disposable, integrated micro-fluidic circuits, typically in credit card-sized cartridges. These micro-fluidic channels were originally developed using microfabrication techniques established within the semiconductor manufacturing industry. Micro-fluidic channels, on the order of hundreds of microns in diameter, are now easily fabricated on silicon chips and other substrates. Fluids flowing in these small channels have unique characteristics that can be applied to different detection methodologies, including cell and separation without centrifugation or filtration. The miniaturization of these processes ensures that minimal volumes of reagents will be needed, minimal volumes of sample will be required, and minimal volumes of waste will be generated.

These micro-fluidic systems are ideal for detecting a substance in the same instrument in which a sample has been collected, eliminating the need to transport the sample to a centralized laboratory, and providing immediate or real time results. The O.R.C.A. µFluidics™ product line of Micronics, Inc. is particularly well suited for use with personal air-monitoring unit 10a. The card-based detection system used in this product usually includes a standard sample input port, one or more reagent introduction ports (not shown), sample storage structures, and waste compartments, and may also contain various micro-fluidic separation and detection channels, incubation areas, micro-fluidic reactors, and valves, details of which are not specifically illustrated.

With respect to FIG. 5, detection unit 64 is exemplary of the O.R.C.A. µFluidics™ product line. It should be noted that the specific internal layout of a detection unit adapted to detect nerve gas might be quite different than that of a detection unit intended to detect another type of chemical or biological agent, and the internal design of detection unit 64 is for illustrative purposes only. Regardless of the specific internal design used in the detection unit, each different type of detection unit will include standard interface port to enable samples to be introduced into the detection unit, as well as to enable a result to be displayed. It is anticipated that when the target particulate is a biological organism or pathogen, flow cytometry (the counting and characterization of biological cells) will be a preferred detection methodology employed in detection unit 64. It is further anticipated that immuno assay and nucleic acid base detection methods can be employed in a micro-fluidic or other portable and disposable detection unit.

Referring once again to FIG. 5, detection unit 64 is inserted into a slot 66 in primary housing 12. Preferably slot 66 is disposed above the batteries inside primary housing 12, although the specific disposition of the slot is not critical. A display 68 is provided on personal air-monitoring unit 10a so that the result of the analysis and detection process carried out by detection unit 64 is displayed to a user. A plurality of controls 70 are further provided to enable a user to activate detection unit 64 after a desired sampling period has been completed. It is also contemplated that display 68 could be incorporated onto detection unit 64, although such an embodiment would likely increase the cost of each disposable detection unit 64. While not separately shown, it should be understood that disposable sample collection cartridge 16 will include a fluid port through which the rinse fluid that has removed particulates from combined impact collector and fan 16c will flow. Furthermore, personal air-monitoring unit 10a includes fluid lines (not shown) that enable detection unit 64 to be connected to disposable sample collection cartridge 16 to receive the liquid sample in sample input port 65 of detection unit 64.

It should be noted that portable sampling units incorporating combined impact collectors and fans in accord with the present invention could be integrated with other types of detector units. The micro-fluid based detectors discussed above are merely exemplary, and should not be considered limiting on the present invention. Other suitable detection units are likely to include color change based test strips, such as those available from Tetracore, Inc. (Gaithersburg, Md.) for determining the presence of anthrax, and sensor-on-a-chip technologies that are available from a number of different companies (for example, see http://www.taosinc.com/pressrelease_sensor.htm). It is anticipated that immuno-assay based detection systems, such as cytometry and fluorescence based systems, and nucleic acid based detection systems will be particularly useful.

Portable Area Air-Monitoring Embodiment

FIGS. 6A, 6B, 7, 8A, 8B, and 9 illustrate aspects of air-monitoring units 100 and 100a that are also portable, but are more rugged than personal air-monitoring units 10 and 10a. These more rugged air-monitoring units 100 and 100a are designed to be extremely durable, and are particularly well suited to be used in emergency response situations by fire fighters and personnel responding to incidents in which potentially hazardous materials may have been released into the environment. While air-monitoring units 100 are 100a is are functionally similar to personal air-monitoring units 10 and 10a in that they all include a combined impact collector and fan, the combined impact collector and fan elements in the more rugged air-monitoring units are designed to be permanent components rather than disposables. These larger, more rugged air-monitoring units include appropriate valves, fluid lines and a pump (note that these elements were incorporated into the rinse station used in connection with the smaller personal air-monitoring unit 10 described above). These units are particularly well suited to obtain samples from areas containing suspected hazards, such as rooms or vehicles. A disposable fluid cartridge 120 used with air-monitoring unit 100 provides a rinse fluid, as well as a rinse fluid reservoir 122a for the sample collected when the combined impact collector and fan is rinsed. Because the combined impact collector and fan is continually reused, the disposable fluid cartridge preferably includes a decontaminating solution as well, so that the combined impact collector and fan, as well as the internal fluid lines, can be cleaned after or before each successive sample is collected.

Figure 6A:
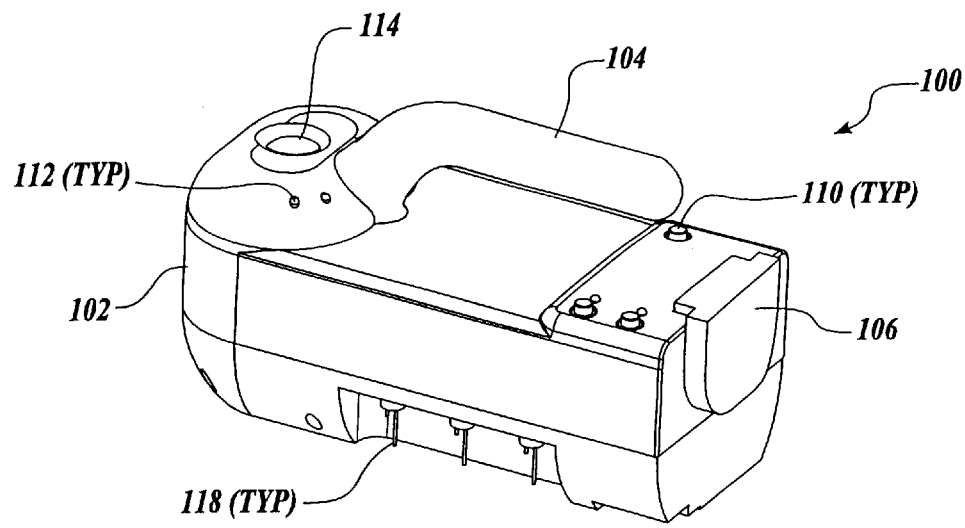

Referring now to FIG. 6A, air-monitoring unit 100 includes a rugged, high impact and waterproof housing 102 that encloses all of the components of the air-monitoring unit. Because this air-monitoring unit was designed to be used by fire fighters and other emergency response personnel, ruggedness and waterproof housing qualities were key functional design objectives. It should be understood that for other applications, a waterproof or extremely rugged housing might not be required. Housing 102 includes an integral handle 104. Note that the size and shape of handle 104 has been ergonomically chosen to accommodate the hand of a user wearing bulky protective gloves. While not shown, a plurality of attachment points are preferably included in housing 102 to enable a variety of different carrying straps to be used transporting air-monitoring unit 100. Despite its relatively small size, its robust construction results in a surprisingly heavy unit, so carrying straps are quite useful.

Air-monitoring unit 100 is designed to be energized by rechargeable batteries. A battery access cover 106 enables batteries to be changed as required. While many types of batteries can be employed, air-monitoring unit 100 has been specifically designed to use lead acid rechargeable batteries that are commonly used to energize professional quality audio-visual equipment. These batteries are readily available, extremely durable, and can be charged and discharged many times before they need to be replaced.

A plurality of user activatable controls 110 are provided. Preferably these controls comprise waterproof switches that require a significant amount of force to actuate, to prevent accidental activation of the controls. As noted above, it is anticipated that users will frequently be wearing bulky protective gloves, so sufficient space is provided between the controls to enable any control to be actuated without accidentally actuating an adjacent control. Of the three control switches shown, preferably one energizes the unit, a second control switch executes a decontamination cycle, and a third control switch initiates a sample collection. A plurality of indicator lights 112 are also provided. Preferably, one indicator light verifies that the unit is energized, and a second indicator light alerts a user if an operational error is detected.

The combined impact collector and fan included in air-monitoring unit 100 cannot be seen in the external view. A fluid inlet 114 enables particulate-laden air to enter the unit. A fluid outlet (not visible in the view of FIG. 6A) is also provided at the front of the unit, to enable sampled air to escape after most of the particulates have been removed.

Figure 6B:
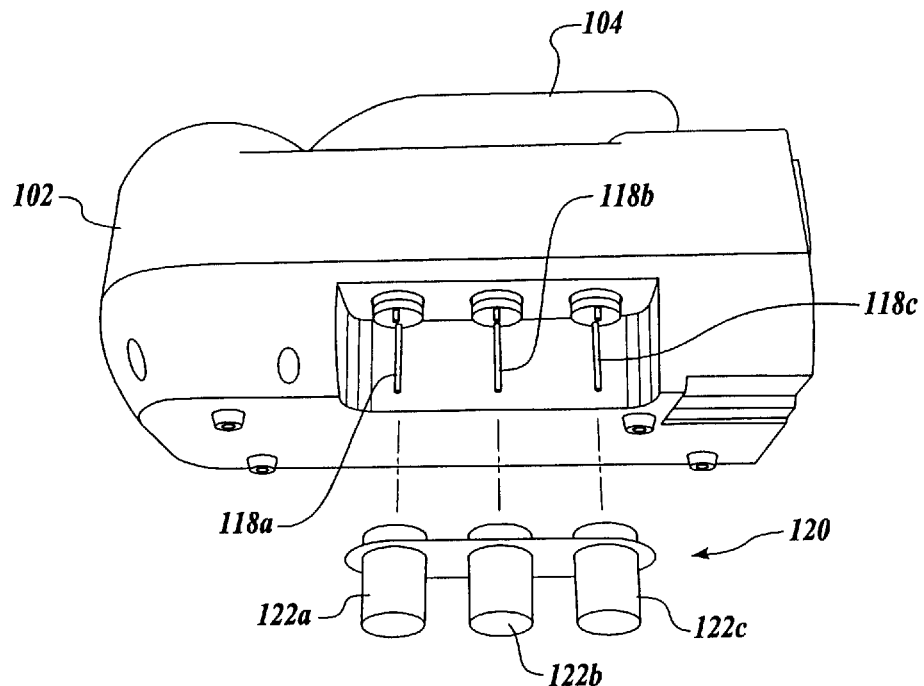
Figure 7:
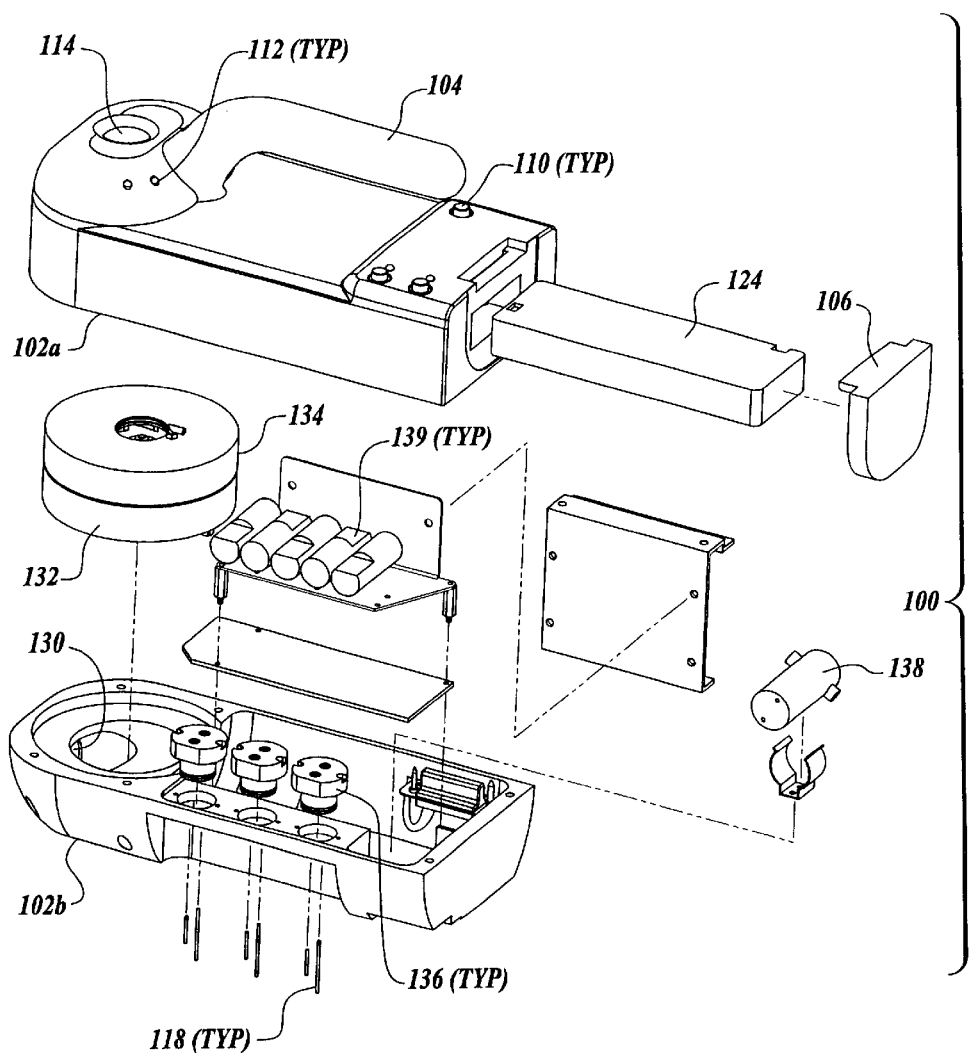

A plurality of fluid tubes or ports 118 are disposed on the left side of air-monitoring unit 100. These fluid ports convey the rinse fluid, decontamination fluid, and particulate-laden rinsate, which is collected in a disposable fluid cartridge. FIG. 6B provides a clearer view of fluid ports 118, as well as disposable fluid cartridge 120. A rinse fluid port 118b is in fluid communication with rinse fluid reservoir 122b when disposable fluid cartridge 120 is properly coupled to air-monitoring unit 100. A plurality of elastomeric sealing surfaces are disposed adjacent to fluid ports 118, to enable disposable fluid cartridge 120 to securely couple to air-monitoring unit 100 without leaking any fluid from the reservoirs.

Preferably the rinse fluid includes a wetting agent to reduce liquid surface tension of the rinse fluid and to increase the effectiveness of the rinse. As noted above, if a biological organism is the target particulate, and culturing will be employed as the detection method, then preferably, the rinse fluid used will not be toxic to the biological organism of interest. Phosphate buffer solutions are generally non-toxic to biological particulates and will typically be used in this case. Also as noted above with respect to the personal air monitoring embodiment, the use of a heated rinse fluid may be desirable in cold climates. Either a heater (not separately shown) can be incorporated into air-monitoring unit 100, or disposable fluid cartridge 120 can be warmed before use.

Once the combined impact collector and fan has been properly rinsed, the rinsate (including the particulates removed by the rinsing process) are delivered to a sample reservoir 122*c* in disposable fluid cartridge 120 via a fluid port 118*c*. Note that when disposable fluid cartridge 120 is initially coupled to air-monitoring unit 100, sample reservoir 122*c* is empty and will preferably be sterile.

Because the combined impact collector and fan of air-monitoring unit 100 is not disposable, it is preferable for the combined impact collector and fan, and any associated fluid lines, to be decontaminated in between sampling sessions, to avoid potential cross contamination of samples. When disposable fluid cartridge 120 is coupled to air-monitoring unit 100, fluid port 118*a* is in fluid communication with a decontamination fluid reservoir 122*a*. A biocidal fluid is preferably employed to decontaminate the system. For example, either a bleach solution or a hydrogen peroxide solution (the commonly available 3% solution is adequate) is utilized as a decontamination fluid. Other protein/nucleic acid decomposing fluids can be similarly employed. It is preferred that the decontamination process be carried out prior to a sample collection (to ensure no contaminants have been picked up during storage of air-monitoring unit 100); however, the decontamination process can instead be executed immediately after sample collection has been completed. Preferably, the biocidal decontamination fluid employed does not interfere with the desired analysis. For example, a peroxide based decontaminating fluid is incompatible with polymerase chain reaction (PCR) assay based detection techniques, and when PCR assay based detection techniques are to be carried out, a non peroxide based decontaminating solution should be utilized.

Alternatively, a first disposable fluid cartridge 120 can be specifically dedicated to rinsing and sampling, while a second disposable fluid cartridge 120 can be specifically dedicated to decontamination. In this scenario, a dedicated sampling fluid cartridge (not separately shown, but identical in appearance to disposable fluid cartridge 120) will have a first fluid reservoir filled with a sterile water solution for a first rinse that is executed prior to the sample collection to ensure that the combined impact collector and fan is clean prior to the sample collection. A second fluid reservoir will contain the rinsing fluid (for removing particulates collected during the sampling period), while a third fluid reservoir will be used for collecting the particulate laden rinsate (the sample). A dedicated decontamination fluid cartridge (also not separately shown, but also identical in appearance to disposable fluid cartridge 120) will have a first fluid reservoir filled with a decontamination fluid for a decontamination flush. A second fluid reservoir will contain a neutralizing solution, which deactivates or neutralizes any residual decontamination fluid. Finally, the third reservoir will contain a sterile water solution for a final rinse. The purpose of the neutralizing solution, and the final rinse, is to ensure that all the decontamination fluid is removed, so that a subsequently collected sample is not adversely affected by an incompatible decontamination fluid.

After air-monitoring unit 100 has rotated the combined impact collector and fan for a desired time period, and the rinsing and decontamination cycles have been completed, the spent disposable fluid cartridge is removed and replaced with a fresh cartridge. The sample contained in the sample reservoir is then delivered to a laboratory (or a field portable analytical station) for analysis. While not individually shown, each fluid reservoir in disposable fluid cartridge 120 preferably includes a leak-proof cap, so that fluids are not spilled when the disposable fluid cartridge is stored or being manipulated. Disposable fluid cartridge 120 is preferably fabricated from a plastic material.

FIG. 7 illustrates further details of air-monitoring unit 100. A rechargeable battery 124 is disposed in an upper housing 102*a*. Sandwiched between upper housing 102*a* and a lower housing 102*b* is a housing 132 in which is disposed a combined impact collector and fan 134 and an electric motor, which is not separately shown. While not specifically shown, it should be understood than the electric motor is electrically coupled to battery 124, and to controls 110 and rotatably drives the combined impact collector and fan to collect particulates, just as explained above in regard to personal air-monitoring units 10 and 10*a*.

Lower housing 102*b* includes a fluid outlet port 130 that enables air drawn into air-monitoring unit 100 via fluid inlet port 114 to be exhausted. A plurality of valves 139 and nozzle manifolds 136 are disposed in lower housing 102*b*, such that each fluid reservoir of disposable fluid cartridge 120 (see FIG. 6B) is serviced by a separate valve/nozzle combination. Each nozzle manifold 136 includes two nozzles, with a separate valve 139 serving each nozzle. The only exception to this is the valve/nozzle combination servicing fluid port 118*b*, which employs a single valve, rather than two valves. This difference arises because fluid port 118*b* is used for the rinse fluid inlet, and the rinse fluid is never reintroduced into rinse fluid reservoir 122*b* via fluid port 118*b* (as the spent rinse fluid is directed to sample reservoir 122*c* via fluid port 118*c*); consequently, a second valve is not required. Two valves are associated with decontamination fluid port 118*a* and sample fluid port 118*c*, such that a flow of fluid entering and exiting the unit in respect to decontamination fluid reservoir 122*a* and sample fluid reservoir 122*c*, can be independently controlled. One valve associated with the nozzle leading to decontamination fluid port 118*a* enables virgin decontamination fluid to enter air-monitoring unit 100, while a second valve associated with the same nozzle returns spent decontamination fluid to decontamination fluid reservoir 122*a*. One valve associated with the nozzle leading to sample fluid port 118*c* enables particulate laden rinse fluid to exit air-monitoring unit 100 and flow into sample reservoir 122*c*, while a second valve associated with the same nozzle enables the sample fluid to be reintroduced into air-monitoring unit 100, either to recycle the rinsate (for embodiments that continually rinse during sampling) or for analysis (i.e., for embodiments described below that incorporate integrated detection units). Preferably, valves 139 are pinch valves.

Also disposed in lower housing 102*b* is a fluid pump 138 that withdraws the rinse fluid from the rinse fluid reservoir of disposable fluid cartridge 120, and pumps the rinse fluid into combined impact collector and fan 134 to rinse particulates from the surfaces of the combined impact collector and fan. Pump 138 is also employed to pump decontamination fluid from the decontamination fluid reservoir in disposable fluid cartridge 120, applying the decontamination fluid to combined impact collector and fan 134, to decontaminate the unit between successive sampling cycles. Finally, pump 138 is employed to ensure that all rinse fluid used to rinse combined impact collector and fan 134 is transferred to sample reservoir 122*c* in disposable fluid cartridge 120. While not specifically shown, it should be understood that internal fluid lines are provided to couple combined impact collector and fan 134 in fluid communication with fluid ports 118. Combined impact collector and fan 134 is functionally identical, and structurally similar to combined impact collector and fan 16*c* of personal air-monitoring unit 10 and 10*a*. However, because combined impact collector and fan 134 is not required to be magnetically coupled to the electric motor that rotates it, it does not include any ferromagnetic element. Also, because combined impact collector and fan 134 is intended to be a permanent and integral component that will be frequently decontaminated, the material from which combined impact collector and fan 134 is fabricated must be able to endure such an extended life that can endure thousands of cycles. A preferred material for the combined impact collector is Altem™ or Teflon embedded Delrin™.

Figure 8A:
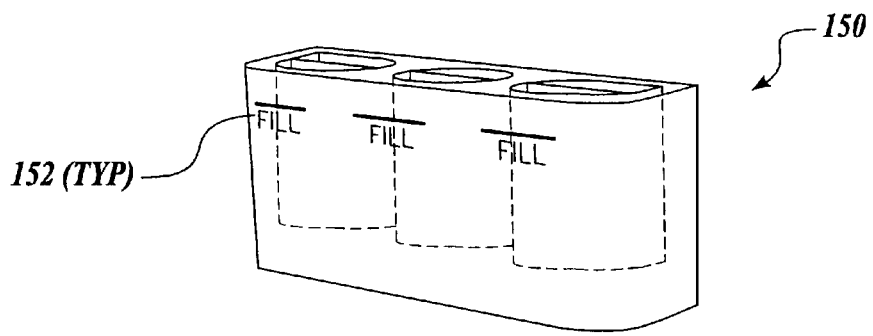
Figure 8B:
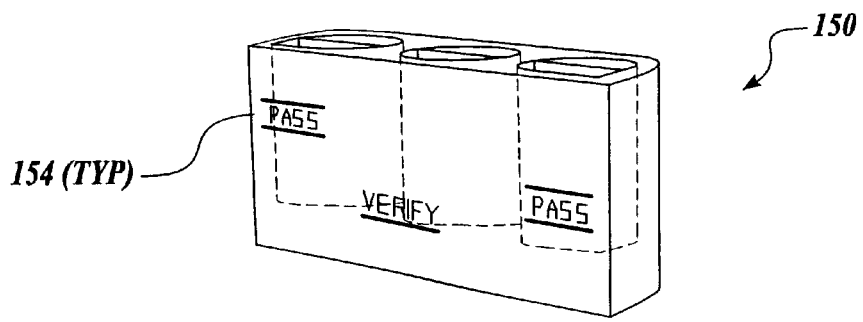

In addition to disposable fluid cartridges 120, a diagnostic cartridge 150 is preferably provided with air-monitoring unit 100. The diagnostic cartridge is shown in FIGS. 8A and 8B and its function is to serve as a tool that can be periodically used to ensure that the fluidic components of air-monitoring unit 100 are functioning properly. The principle embodied in diagnostic cartridge 150 is simple. A known volume of fluid is injected into air-monitoring unit 100 during a test rinse cycle. The volume of fluid captured after the completion of the rinse cycle is then measured to determine if any fluid loss is within acceptable limits. To use diagnostic cartridge 150, a user fills the cartridges corresponding to the disposition of rinse reservoir 122*a* and decontamination fluid reservoir 122*b* with a fluid (preferably sterile water, or a specialized cleaning fluid that includes surfactants) to a level indicated by fill lines 152. Note that one side of diagnostic cartridge 150 is marked with fill lines 152 (FIG. 8A), while the opposite side of diagnostic cartridge 150 is marked with a plurality of pass lines 154. Once diagnostic cartridge 150 is properly filled and inserted into air-monitoring unit 100 (in the same location and fashion that disposable fluid cartridge 120 is connected), the user initiates a test sampling cycle. At the end of the test sampling cycle, the user examiners the level of fluid returned to diagnostic cartridge 150 relative to pass lines 154. If the level of fluid is within the pass marks, the unit is functioning properly. If the fluid levels are not within the pass marks, this indicates that the unit is not functioning properly and that air-monitoring unit 100 should be removed from service until repaired.

Figure 9:
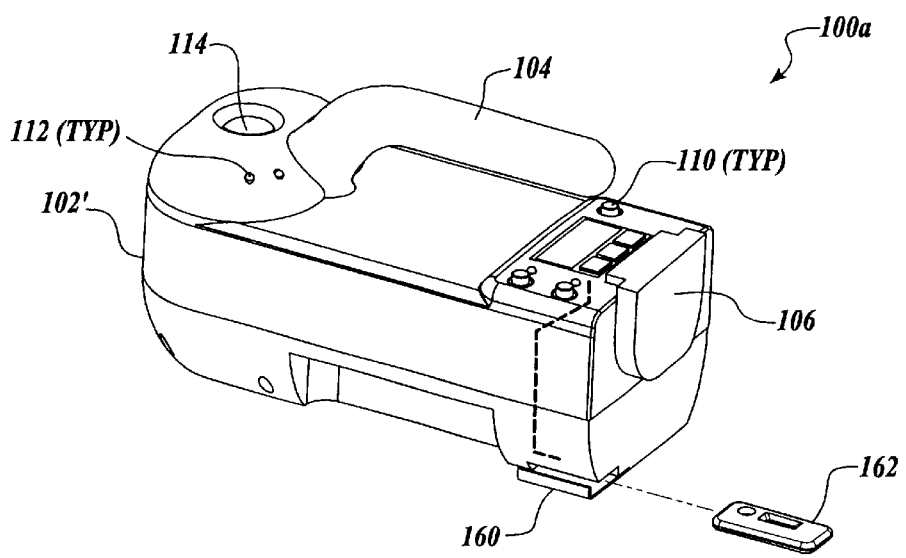

FIG. 9 illustrates an air-monitoring unit 100*a* that has been modified to incorporate a real time detection unit 162. A housing 102' includes a slot 160. Preferably, housing 102' similarly includes an upper housing and a lower housing, as described above with respect to air-monitoring unit 100. As shown in FIG. 9, slot 160 is disposed in a lower housing portion of housing 102', although it should be understood that slot 160 could also be disposed in an upper housing portion of housing 102'. The purpose of slot 160 is to provide a recess into which detection unit 162 is inserted. Detection unit 162 might be designed to detect the presence of anthrax as evident from a color change appearing on a portion of the detection unit. After air-monitoring unit 100*a* has been operated for the desired time period, and a sample has been obtained in the sample reservoir of disposable fluid cartridge 120, a small amount of sample fluid is placed into detection unit 162. A specific color change on the detection unit indicates the presence of anthrax. An anthrax detection unit is readily available from Tetracore, Inc. Similar color change detection units for other agents are also available from the same company.

It should be noted that it is contemplated that other types of real time detection units can be integrated into portable air-monitoring unit 100*a*, and that the use of the anthrax detection unit described above is merely exemplary, and should not be considered limiting on the scope of the invention. For example, it is anticipated that the micro-fluidic, card-based detection units described above in conjunction with personal air-monitoring unit 10*a* could be incorporated into portable air-monitoring unit 100*a*. Of course, housing 102 would need to be modified to provide a slot for such a micro-fluidic card. Furthermore, in such an embodiment it would likely be preferable to change the path of the fluid line connecting combined impact collector and fan 134 to fluid port 118*c*, such that the sample fluid was directed instead to the micro-fluidic card. In such a case, either a portion of the sample fluid could be directed into the sample reservoir of disposable fluid cartridge 120 for archival purposes (or confirmation of results at a later time), or all of the sample fluid could be directed to the micro-fluidic card. Of course, as with personal air-monitoring unit 10*a*, other portable detection technologies readily adaptable to be employed as a disposable unit could be integrated into portable air-monitoring unit 100*a*.

It should be noted that portable air-monitoring units 100 and/or 100*a* can be adapted to operate according to several different sampling paradigms. As described above, the combined impact collector and fan is rotated for a defined period of time, and then rinsing is initiated once the combined impact collector and fan stops rotating. It is contemplated that portable air-monitoring units 100 and/or 100*a* can be automatically programmed to selectively operate for one of several different sampling cycle times, under the control of a programmable electronic controller that is included therein. Each different predefined sampling time cycle will be optimized for collecting a specific particulate.

In one contemplated embodiment, the rinse fluid reservoir and sample reservoir of the disposable fluid cartridge are combined, such that while the combined impact collector and fan is rotating, it is rinsed with the rinse fluid previously used. In such an embodiment, the rinse fluid is thus continually recycled and the concentration of the particulates in the rinse fluid will increase if the air drawn into the collector continues to include the particulates. It is further contemplated that a relatively large volume of rinse fluid can be provided (along with a correspondingly large sample reservoir), such that any time the combined impact collector and fan is rotating, fresh rinse fluid is used to rinse the combined impact collector and fan. Such a non re-circulated rinse is best for maintaining cell viability, which is critical if culturing techniques are employed in the detection method. A non re-circulated rinse is also preferable if a continuous sample feed is provided to the detector for ongoing, real time detection.

It is further anticipated that combined impact collector and fan 134 can be coated with a substance that increases the adhesion of particulates when in a first state (i.e., when in a dry state) and which enhances the removal of particulates in a second state (i.e., when in a wet state). One such type of coating undergoing empirical testing is a mixture of sugar and gelatin.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

What is claimed is:

1. A method for separating particulates from a gaseous fluid, comprising the steps of:
   (a) providing a combined impact collector and fan disposed within a cavity having a port, said combined impact collector and fan being rotatable about an axis;
   (b) rotating the combined impact collector and fan about the axis;
   (c) drawing the gaseous fluid carrying the particulates into the cavity by causing the combined impact collector and fan to rotate;
   (d) separating the particulates from the gaseous fluid by impacting them with the combined impact collector and fan as it rotates such that the particulates adhere ti the combined impact collector and fan while in a dry state;
   (e) after sufficient particulates have adhered to the combined impact collector and fan, rinsing the combined impact collector and fan with a rinse liquid; and
   (f) collecting a rinsate produced by rinsing said combined impact collector and fan, said rinsate comprising said rinse liquid and said particulates.

2. The method of claim 1, wherein the step of rinsing comprises the step of rinsing the combined impact collector and fan with a rinse liquid while said combined impact collector and fan is rotating.

3. The method of claim 1, wherein the step of collecting a rinsate comprises the step of directing said rinsate into a rinse liquid reservoir, such that said rinse fluid is recycled and again used for rinsing said combined impact collector and fan.

4. The method of claim 1, wherein the step of rinsing comprises the step of rinsing the combined impact collector and fan with a predefined volume of rinse fluid after said combined impact collector and fan has been rotated for a predefined period of time.

5. The method of claim 4, wherein said predefined period of time is determined as a function of the type of particulate being collected.

6. The method of claim 1, wherein the step of rinsing comprises utilizing a rinse liquid that is not toxic to biological particulates, said method further comprising the step of thus enabling a collected sample to be cultured to determine a result.

7. The method of claim 1, wherein the step of rinsing comprises utilizing at least one of a rinse liquid that includes a surfactant to reduce a surface tension of said rinse liquid, and a heated rinse liquid, thereby increasing an efficiency with which particulates are rinsed from the combined impact collector and fan.

8. The method of claim 1, further comprising the step of stopping the rotation of said combined impact collector and fan before the step of rinsing.

9. The method of claim 8, further comprising the steps of removing said combined impact collector from a prime mover after stopping its rotation and before the step of rinsing.

10. The method of claim 9, further comprising the step of providing a rinse station, wherein the step of rinsing comprises the step of placing said combined impact collector in said rinse station.

11. The method of claim 10, further comprising the step of providing a rinse cassette, wherein the step of placing said combined impact collector into said rinse station comprises the steps of inserting said combined impact collector and fan into said rinse cassette; and then placing said rinse cassette in said rinse station.

12. The method of claim 11, wherein the step of rinsing further comprises the step of rotating said combined impact collector and fan within said rinse cassette during rinsing, to aid in removing said particulates from said combined impact collector.

13. The method of claim 11, wherein the step of rinsing further comprises the step of applying an ultrasonic pulse to said rinse cassette during rinsing, to aid in removing said particulates from said combined impact collector.

14. The method of claim 1, further comprising the steps of providing a biocidal decontamination fluid; and flushing said combined impact collector and fan and said cavity with said biocidal decontamination fluid before the step of rotating said combined impact collector.

15. The method of claim 14, wherein the biocidal decontamination fluid comprises at least one of a bleach solution, a hydrogen peroxide solution, a protein decomposing solution, and a nucleic acid decomposing solution.

16. The method of claim 14, wherein the biocidal decontamination fluid comprises a fluid that does not interfere with a selected detection method.

17. The method of claim 14, wherein the step of flushing comprises the step of flushing any fluid lines that are in fluid communication with said combined impact collector and fan and said cavity with the biocidal decontamination fluid.

18. The method of claim 14, wherein the step of flushing comprises the step of collecting spent biocidal decontamination fluid produced by said step of flushing, in a spent biocidal decontamination fluid reservoir.

19. The method of claim 14, further comprising the steps of providing a neutralizing fluid; and flushing said combined impact collector and fan and said cavity with said neutralizing fluid, after the step of flushing with said biocidal decontamination fluid, and before the step of rotating said combined impact collector.

20. The method of claim 19, further comprising the steps of providing a sterile fluid; and flushing said combined impact collector and fan and said cavity with said sterile fluid, after the step of flushing with said neutralizing fluid, and before the step of rotating said combined impact collector.

21. The method of claim 1, further comprising the step of enabling a user to selectively control a length of time during which said combined impact collector and fan is rotating.

22. The method of claim 21, further comprising the step of enabling a user to selectively control a manner in which the step of rinsing is carried out, including at least one of the following:

(a) rinsing while said combined impact collector and fan is rotating;

(b) rinsing after said combined impact collector has stopped rotating;

(c) rinsing with said rinsate, thereby recycling the rinsate; and (d) rinsing for a time period selected by a user.

23. The method of claim 1, further comprising the step of enabling a user to control a decontamination of the combined impact collector and fan and of the cavity, by enabling the user to select at least one of the following options:
   (a) decontaminating said combined impact collector and fan and said cavity prior to the step of rotating said combined impact collector;
   (b) decontaminating said combined impact collector and fan and said cavity after the step of rinsing and after said rinsate has been collected; and
   (c) decontaminating said combined impact collector and fan and said cavity after a predefined number of cycles of the step of rotating, rinsing and collecting have occurred.

24. The method of claim 14, further comprising the step of furnishing said combined impact collector, said cavity, a biocidal decontamination fluid reservoir, a rinse fluid reservoir, and a rinsate collection reservoir as an integrated unit.

25. The method of claim 1, further comprising the steps of providing an analytical unit for use in testing said rinsate.

26. The method of claim 25, wherein said analytical unit is capable of detecting anthrax.

27. The method of claim 25, wherein said analytical unit comprises a disposable unit specifically adapted to detect a specific particulate.

28. The method of claim 25, wherein said analytical unit comprises a disposable micro-fluidic unit.

29. The method of claim 25, wherein said analytical unit uses a immunoassay-based detection system.

30. The method of claim 29, wherein said immunoassay-based detection system comprises at least one of a cytometry based detection system and a fluorescence-based detection system.

31. The method of claim 25, wherein said analytical unit uses a nucleic acid-based detection system.

32. A portable impact particle collector for separating particulates from a gaseous fluid in which the particulates are entrained, comprising:
   (a) a prime mover having a drive shaft that is drivingly rotated;
   (b) a power supply that energizes said prime mover;
   (c) a primary housing substantially enclosing said prime mover and said power supply;
   (d) a combined impact collector and fan that is coupled to said drive shaft and is drivingly rotated thereby within a cavity;
   (e) an inlet port through which said gaseous fluid in which the particulates are entrained is drawn into said cavity by rotation of the combined impact collector and fan, said combined impact collector and fan collecting said particulates entrained in the gaseous fluid as they impact upon surfaces of the combined impact collector and fan that is rotating, and are retained thereon thereby separating said particulates from the gaseous fluid;
   (f) at least one of:
      (i) a cassette removably coupled with the primary housing, the cassette encompassing said combined impact collector and fan and defining said cavity, such that the combined impact collector and fan is disposed outside of said primary housing; and
      (ii) means for rinsing the combined impact collector and fan with a stream of a rinse liquid after particulates have been retained upon the combined impact collector and fan, said stream of the rinse liquid removing the particulates from the combined impact collector and fan; and
   (g) a control operatively connected to control actuation of said prime mover with said power supply, adapted to enable a user to selectively energize said prime mover.

33. The portable impact particle collector of claim 32, wherein said combined impact collector and fan comprises a plurality of arcuate-shaped vanes.

34. The portable impact particle collector of claim 32, wherein said combined impact collector and fan includes a ferromagnetic element that is magnetically coupled to the shaft of said prime mover.

35. The portable impact particle collector of claim 32, wherein said primary housing includes surface features that aid in the positioning of said cassette when the cassette is are coupled to the primary housing.

36. The portable impact particle collector of claim 32, further comprising a secondary housing generally covering said cassette.

37. The portable impact particle collector of claim 36, wherein said secondary housing is pivotally connected to said primary housing.

38. The portable impact particle collector of claim 32, cassette and said combined impact collector and fan are disposable, being thereby adapted to be replaced by a user after a defined period of use.

39. The portable impact particle collector of claim 32, wherein said cassette comprises a fluid passage is coupled to said combined impact collector and fan to form an integrated unit.

40. The portable impact particle collector of claim 32, wherein said cassette comprises an upper portion and a lower portion that define the cavity, said combined impact collector and fan being disposed between said upper portion and said lower portion and being freely rotatable therein.

41. The portable impact particle collector of claim 40, wherein at least one of said lower portion and said combined impact collector and fan are fabricated from a self-lubricating material.

42. The portable impact particle collector of claim 32, further comprising an electronic controller electrically coupled to the control and to said prime mover.

43. The portable impact particle collector of claim 32, wherein said combined impact collector and fan comprises a disc having a plurality of arcuate shaped vanes disposed on its upper surface.

44. The portable impact particle collector of claim 32, wherein said combined impact collector and fan is fabricated from a plastic capable of maintaining its structural integrity while being rotated at a speed in excess of five thousand revolutions per minute.

45. The portable impact particle collector of claim 32, wherein said means for rinsing the combined impact collector and fan comprising:
   (a) a rinse liquid reservoir adapted to contain a volume of rinse liquid;
   (b) a first liquid line coupling said rinse fluid reservoir in fluid communication with said combined impact collector and fan;
   (c) a sample collection reservoir that receives the rinse liquid used to rinse particulates from said combined impact collector and fan; and
   (d) a second fluid line coupling said sample collection reservoir in fluid communication with said combined impact collector and fan.

46. The portable impact particle collector of claim 45, further comprising a detection unit that is capable of identifying at least one particulate.

47. The portable impact particle collector of claim 46, wherein said detection unit is capable of detecting a biological pathogen.

48. The portable impact particle collector of claim 46, wherein said detection unit comprises a disposable cartridge incorporating a plurality of micro-fluidic channels.

49. The portable impact particle collector of claim 48, wherein said rinse liquid reservoir and said sample collection fluid reservoir are disposed in said disposable cartridge detection unit.

50. The portable impact particle collector of claim 48, wherein said disposable cartridge detection unit employs at least one of cytometry and fluorescence to identify specific particulates.

51. The portable impact particle collector of claim 45, further comprising a decontamination fluid reservoir, adapted to contain a fluid capable of decontaminating said combined impact collector and fan, and a decontamination fluid line coupling said decontamination fluid reservoir in fluid communication with said combined impact collector and fan.

52. The portable impact particle collector of claim 51, wherein said rinse liquid reservoir, said decontamination fluid reservoir, and said collection fluid reservoir are disposed in a disposable fluid cartridge.

53. The portable impact particle collector of claim 52, wherein said disposable fluid cartridge is disposed outside said primary housing.

54. The portable impact particle collector of claim 52, wherein said first fluid line, said second fluid line, and said decontamination fluid line are disposed within said primary housing.

55. The portable impact particle collector of claim 54, further comprising a plurality of valves, each of which is coupled to one of said first fluid line, said second fluid line, and said decontamination fluid line, to control fluid flow therein.

56. The portable impact particle collector of claim 55, further comprising an electronic controller functionally coupled to said control, said plurality of valves, and said prime mover.

57. The portable impact particle collector of claim 52, further comprising a diagnostic cartridge, adapted to providing an indication of whether said portable impact particle collector is functioning properly.

58. The portable impact particle collector of claim 57, wherein said diagnostic cartridge comprises a plurality of fluid reservoirs, at least some of which include markings that indicate whether an expected volume of fluid has been processed by the portable impact particle collector based upon a fluid level in the plurality of fluid reservoirs.

59. The portable impact particle collector of claim 45, wherein said rinse liquid reservoir and said sample collection reservoir are combined into a single reservoir, so that a rinse liquid is recycled.

60. The portable impact particle collector of claim 45, further comprising a plurality of valves coupled to said rinse liquid reservoir and said sample collection reservoir, such that a flow of liquid from said rinse fluid reservoir and into said sample collection reservoir is selectively controlled.

61. The portable impact particle collector of claim 45, further comprising a pump that draws rinse liquid from said rinse fluid reservoir and forces said rinse liquid onto said combined impact collector and fan through the first fluid line.

62. The portable impact particle collector of claim 61, wherein said pump further draws rinse liquid from said combined impact collector and fan and forces said fluid into said sample collection reservoir through said second fluid line.

63. The portable impact particle collector of claim 61, wherein the pump is driven by the prime mover.

64. The portable impact particle collector of claim 61, wherein the pump is driven independently of the prime mover.

65. The portable impact particle collector of claim 45, wherein said rinse liquid comprises water.

66. The portable impact particle collector of claim 65, wherein said rinse liquid further comprises a surfactant to reduce surface tension, and thus, to enhance the removal of particulates adhering to said combined impact collector and fan.

67. The portable impact particle collector of claim 65, wherein said rinse liquid further comprises a phosphate buffer solution.

68. The portable impact particle collector of claim 51, wherein the decontamination fluid comprises at least one of a hydrogen peroxide solution and a bleach solution.

69. The portable impact particle collector of claim 32, wherein the gaseous fluid comprises air that is sampled from an ambient environment.

70. The portable impact particle collector of claim 32, wherein said combined impact collector and fan is coated with a substance to which the particulates adhere when the substance is dry, said substance releasing the particulates when wetted with the rinse liquid.

71. The portable impact particle collector of claim 70, wherein said substance comprises at least one of gelatin and sugar.

72. A portable system for separating particulates from a gaseous fluid, and testing said particulates to determine if a specific type of particulate has been separated from said gaseous fluid, comprising:
  (a) a portable combined impact collector and fan-based sampling unit that separates particulates from a fluid, said sampling unit comprising:

(i) a fluid passage for conveying said gaseous fluid in which the particulates are entrained, said fluid passage having an inlet and an outlet;

(ii) a rotatably driven combined impact collector and fan disposed within said fluid passage, such that rotation of said combined impact collector and fan both draws the gaseous fluid into the fluid passage toward said combined impact collector and fan, and collects said particulates entrained in the gaseous fluid as they impact upon dry surfaces of the combined impact collector and fan, thereby separating said particulates from the gaseous fluid;

(iii) a prime mover having a drive shaft that is drivingly coupled to said combined impact collector and fan, said combined impact collector being rotated thereby;

(iv) a power supply electrically coupled to said prime mover, said power supply energizing said prime mover;

(v) a primary housing substantially enclosing said prime mover and said power supply;

(vi) means for rinsing the surfaces of the combined impactor collector and fan with a stream of a rinse liquid after the particulates have been retained upon the surfaces of the combined impactor collector and fan, thereby removing the particulates that were thus collected from the surfaces of the combined impactor collector and fan with the stream of rinse liquid; and (b) a detection unit capable of identifying a specific particulate that has been separated from said gaseous fluid.

73. The portable system of claim 72, wherein said detection unit detects at least one of a biological pathogen, a biological toxin, an allergen, a mold, and a fungi.

74. The portable system of claim 72, wherein said detection unit comprises a plurality of micro-fluidic channels.

75. The portable system of claim 72, wherein said detection unit employs at least one of cytometry, immuno assay, and nucleic acid based detection for detecting the specific particulate.

76. The portable system of claim 72, wherein said detection unit comprises a disposable detection cartridge.

77. The portable system of claim 72, wherein said fluid passage and said combined impact collector and fan comprise a disposable sample cartridge.

78. The portable system of claim 77, wherein said combined impact collector and fan is magnetically coupled to said prime mover.

79. The portable system of claim 77, wherein said disposable sample cartridge is disposed outside said primary housing.

80. The portable system of claim 77, further comprising a rinse cartridge into which said disposable sample cartridge is placed after particulates have been separated from said gaseous fluid and before said means for rinsing has removed the separated particles from the surface of the combined impact collector and fan, and said detection unit has analyzed the separated particulates.

81. The portable system of claim 80, wherein said rinse cartridge comprises a pinch valve that prevents a rinsate from being discharged from the rinse cartridge until said pinch valve is actuated.

82. The portable system of claim 81, wherein said rinse cartridge has an interior volume that is larger than an external volume of said disposable sample cartridge, such that only a predefined volume of rinse liquid can be added to said rinse cartridge after a disposable sample cartridge is inserted into said rinse cartridge.

83. The portable system of claim 82, wherein said predefined volume of rinse liquid comprises less than five milliliters.

84. The portable system of claim 77, wherein said means for rinsing comprises a rinse station for producing a liquid sample containing particulates collected by said disposable sample cartridge.

85. The portable system of claim 84, wherein said rinse station comprises a lateral flow disc for collecting said liquid sample.

86. The portable system of claim 84, wherein said rinse station comprises an ultrasonic unit for applying ultrasonic waves to said disposable sample cartridge, to aid in removing particulates from said combined impact collector and fan.

87. The portable system of claim 84, wherein said rinse station comprises a prime mover for rotating said combined impact collector and fan portion of said disposable sample cartridge, to aid in removing particulates from said combined impact collector and fan.

88. The portable system of claim 84, wherein said rinse station comprises a vibrating unit for vibrating said disposable sample cartridge, to aid in removing particulates from said combined impact collector and fan.

89. The portable system of claim 84, wherein said rinse station comprises:

(a) a rinse liquid reservoir adapted to store a volume of rinse liquid;

(b) a disposable sample cartridge holder that secures said disposable sample cartridge during rinsing;

(c) a rinse fluid line coupling said rinse liquid reservoir in fluid communication with said disposable sample cartridge holder, such that a desired volume of rinse fluid is delivered to said disposable sample cartridge holder;

(d) a pump that delivers the desired volume of rinse liquid from said rinse liquid reservoir to said disposable sample cartridge holder, said pump being coupled in fluid communication with said rinse liquid reservoir and said rinse fluid line; and (e) a liquid sample collection reservoir that collects a rinsate from said disposable sample cartridge holder, said rinsate including particulates that were collected by said combined impact collector and fan, said liquid sample collection reservoir being in fluid communication with said disposable sample cartridge holder.

90. The portable system of claim 72, wherein said means for rinsing comprises:

(a) a rinse liquid reservoir adapted to contain a volume of rinse liquid;

(b) a first fluid line coupled in fluid communication with said rinse liquid reservoir and said combined impact collector and fan;

(c) a sample collection reservoir that is sized to contain a volume of rinse fluid used to rinse particulates from said combined impact collector and fan; and (d) a second fluid line in fluid communication with said sample collection reservoir and said combined impact collector and fan.

91. The portable system of claim 90, wherein said means for rinsing further comprises a decontamination fluid reservoir sized to contain a fluid used for decontaminating said combined impact collector and fan, and a decontamination fluid line in fluid communication with said decontamination fluid reservoir and said combined impact collector and fan.

92. The portable system of claim 91, wherein said rinse liquid reservoir, said decontamination fluid reservoir, and said collection fluid reservoir are disposed in a disposable fluid cartridge.

93. The portable system of claim 92, wherein said disposable fluid cartridge is disposed outside said primary housing.

94. The portable system of claim 91, wherein said first fluid line, said second fluid line, and said decontamination fluid line are disposed within said primary housing.

95. The portable system of claim 91, wherein said means for rinsing further comprises a plurality of valves coupled to said first fluid line, said second fluid line and said decontamination fluid line, to independently control fluid flow therein.

96. The portable system of claim 91, wherein said means for rinsing further comprises an electronic controller functionally coupled to at least one control, said plurality of valves, and said prime mover.

97. The portable system of claim 91, wherein said means for rinsing further comprises a diagnostic cartridge used to indicate whether said portable system is functioning properly.

98. The portable system of claim 97, wherein said diagnostic cartridge comprises a plurality of fluid reservoirs, at least some of which include markings that indicate an expected minimum volume of fluid that should be in the fluid reservoirs if the portable system is operating properly.

99. The portable system of claim 91, wherein said rinse liquid reservoir and said sample collection reservoir are combined into a single reservoir to hold a rinse liquid that is recycled.

100. The portable system of claim 91, wherein said means for rinsing further comprises a pump that draws liquid from said rinse liquid reservoir and forces said fluid onto said combined impact collector and fan through the first liquid line.

101. The portable system of claim 100, wherein said pump is further capable of drawing liquid from said combined impact collector and fan and forcing said liquid into said sample collection reservoir through said second fluid line.

* * * * *

UNITED STATES PATENT AND TRADEMARK OFFICE
CERTIFICATE OF CORRECTION

PATENT NO. : 6,729,196 B2
DATED : May 4, 2004
INVENTOR(S) : Moler et al.

It is certified that error appears in the above-identified patent and that said Letters Patent is hereby corrected as shown below:

Column 19,
Line 28, "ti" should read -- to --
Line 48, "fluid" should read -- liquid --

Column 22,
Line 15, after "is" delete "are"
Line 23, after "claim 23," insert -- wherein said --
Line 28, after "passage" delete "is coupled to said combined impact collector and fan to form an integrated unit"
Line 55, "liquid" should read -- fluid --

Column 23,
Line 63, "fluid" should read -- liquid --

Column 24,
Line 1, "combined impact collector and fan" should read -- cavitiy --
Line 1, after "said" delete "fluid" and insert therefor -- rinse liquid --

Column 26,
Line 32, "fluid" should read -- liquid --

Column 28,
Line 1, "fluid" should read -- liquid --
Line 2, "liquid" should read -- fluid --

Signed and Sealed this

Fifteenth Day of March, 2005

JON W. DUDAS
*Director of the United States Patent and Trademark Office*